US011279818B2

(12) United States Patent
Kageyama et al.

(10) Patent No.: US 11,279,818 B2
(45) Date of Patent: Mar. 22, 2022

(54) RUBBER COMPOSITION, HETEROCYCLE-MODIFIED GLYCERIN FATTY ACID ESTER, AND PRODUCTION METHOD FOR HETEROCYCLE-MODIFIED GLYCERIN FATTY ACID ESTER

(71) Applicant: THE YOKOHAMA RUBBER CO., LTD., Tokyo (JP)

(72) Inventors: Hirokazu Kageyama, Hiratsuka (JP); Kazushi Kimura, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 210 days.

(21) Appl. No.: 16/756,618

(22) PCT Filed: Oct. 23, 2018

(86) PCT No.: PCT/JP2018/039378
§ 371 (c)(1),
(2) Date: Apr. 16, 2020

(87) PCT Pub. No.: WO2019/082900
PCT Pub. Date: May 2, 2019

(65) Prior Publication Data
US 2020/0255636 A1 Aug. 13, 2020

(30) Foreign Application Priority Data

Oct. 24, 2017 (JP) .............................. JP2017-205374

(51) Int. Cl.
*C08L 9/06* (2006.01)
*C08K 3/36* (2006.01)
*C08K 5/3462* (2006.01)
*C08K 5/357* (2006.01)
*C08K 5/46* (2006.01)

(52) U.S. Cl.
CPC .................. *C08L 9/06* (2013.01); *C08K 3/36* (2013.01); *C08K 5/3462* (2013.01); *C08K 5/357* (2013.01); *C08K 5/46* (2013.01); *C08L 2205/02* (2013.01)

(58) Field of Classification Search
CPC ......... C08K 5/3462; C08K 5/357; C08K 5/46
See application file for complete search history.

(56) References Cited

U.S. PATENT DOCUMENTS 7,138,450 B2 * 11/2006 Wentworth .............. C08K 5/10
524/284
2014/0364560 A1 12/2014 Backer et al.

FOREIGN PATENT DOCUMENTS

CN 102212043 B * 4/2013
JP 2015-502357 A 1/2015

* cited by examiner

*Primary Examiner* — Vickey Nerangis
(74) *Attorney, Agent, or Firm* — Carrier Blackman & Associates, P.C.; Joseph P. Carrier; Fulchand P. Shende

(57) ABSTRACT

An object of the present invention is to provide a rubber composition having excellent processability, a heterocycle-modified glycerin fatty acid ester, and a production method for the heterocycle-modified glycerin fatty acid ester. The present invention includes: a rubber composition containing a rubber, silica, and a heterocycle-modified glycerin fatty acid ester, in which an epoxy group is modified with a heterocyclic compound having a heterocycle having at least one H—N< bond, where the heterocycle is at least one selected from the group consisting of a piperazine ring, a morpholine ring, and a thiomorpholine ring, and the heterocycle may have a substituent; the heterocycle-modified glycerin fatty acid ester; and a production method therefor.

5 Claims, No Drawings

RUBBER COMPOSITION, HETEROCYCLE-MODIFIED GLYCERIN FATTY ACID ESTER, AND PRODUCTION METHOD FOR HETEROCYCLE-MODIFIED GLYCERIN FATTY ACID ESTER

TECHNICAL FIELD

The present invention relates to a rubber composition, a heterocycle-modified glycerin fatty acid ester, and a production method for a heterocycle-modified glycerin fatty acid ester.

BACKGROUND ART

In the related art, silica has been widely used in rubber compositions used in a tire in order to reduce a rolling resistance of the tire. Particles of the silica are more likely to aggregate with each other, and a dispersion of the silica in rubber is generally difficult. To improve the dispersibility of the silica, a method for adding a sulfur-containing silane coupling agent has been known.

For example, Patent Document 1 discloses a diene elastomer composition including a diene elastomer, a hydrolysable silane, and a curing agent for the diene elastomer, in which the hydrolysable silane has a particular structure.

CITATION LIST

Patent Literature

Patent Document: JP 2015-502357 T

SUMMARY OF INVENTION

Technical Problem

The present inventors have found, by referring to Patent Document 1, that as a result of preparing a rubber composition containing a hydrolysable silane having a piperazine ring and evaluating the prepared rubber composition, such a composition has a high Mooney viscosity and cannot prevent scorch (burning of unvulcanized rubber), and may have low processability (Comparative Example 2).

Therefore, an object of the present invention is to provide a compound by which a rubber composition achieves excellent processability (e.g. Mooney viscosity is low and Mooney scorch is within an appropriate range).

Furthermore, another object of the present invention is to provide a rubber composition containing the compound and a production method for the compound.

Solution to Problem

As a result of diligent research to solve the problems described above, the present inventors found that a desired effect can be obtained by a heterocycle-modified glycerin fatty acid ester, in which an epoxy group is modified with a heterocycle by a heterocyclic compound having a predetermined heterocycle, and thus completed the present invention.

The present invention is based on the findings described above and, specifically, solves the problem described above by the following features.

[1]
A rubber composition containing:
a rubber;
silica; and
a heterocycle-modified glycerin fatty acid ester, in which an epoxy group is modified with a heterocyclic compound having a heterocycle having at least one H—N< bond, where
the heterocycle is at least one selected from the group consisting of a piperazine ring, a morpholine ring, and a thiomorpholine ring; and
the heterocycle may have a substituent.

[2]
The rubber composition according to [1], where the heterocycle-modified glycerin fatty acid ester has a group represented by Formula (I) below:

[Chemical Formula 1]

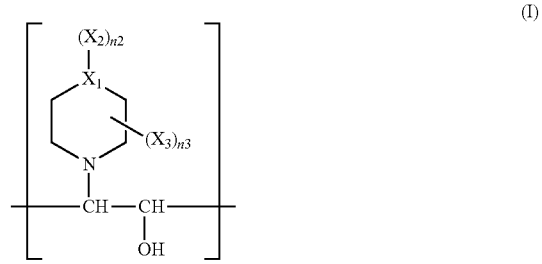

where $X_1$ represents at least one selected from the group consisting of a nitrogen atom, an oxygen atom, and a sulfur atom, $X_3$ represents a hydrocarbon group, and n3 represents from 0 to 4, in the case where $X_1$ is a nitrogen atom, n2 is 1, and $X_2$ represents a hydrogen atom or an organic group, and in the case where $X_1$ is an oxygen atom or a sulfur atom, n2 represents 0.

[3]
The rubber composition according to [2], where,
in Formula (I), $X_1$ is a nitrogen atom,
n2 is 1, and
$X_2$ is at least one selected from the group consisting of a hydrogen atom, a sulfone-based protecting group, a carbamate-based protecting group, and Formula (I-1):
—(R—O)$_{n4}$—H; and
in Formula (I-1), R each independently represents a divalent hydrocarbon group, and n4 represents from 1 to 10.

[4]
The rubber composition according to [2], where, in Formula (I), $X_1$ is an oxygen atom or a sulfur atom, and n2 is 0.

[5]
The rubber composition according to any one of [2] to [4], where a fatty acid constituting the heterocycle-modified glycerin fatty acid ester has a group represented by Formula (I).

[6]
A heterocycle-modified glycerin fatty acid ester, where
an epoxy group is modified with a heterocyclic compound having a heterocycle having at least one H—N< bond;
the heterocycle is at least one selected from the group consisting of a piperazine ring, a morpholine ring, and a thiomorpholine ring; and the heterocycle may have a substituent.

[7]

A production method for a heterocycle-modified glycerin fatty acid ester, where the heterocycle-modified glycerin fatty acid ester described in [6] is produced by reacting an epoxidized glycerin fatty acid ester and the heterocyclic compound.

[8]

The production method according to [7], where the epoxidized glycerin fatty acid ester is an epoxidized vegetal oil.

Advantageous Effects of Invention

The rubber composition of the present invention has the superior workability.

According to the heterocycle-modified glycerin fatty acid ester of the present invention, a rubber composition having excellent processability can be obtained.

According to the production method of the present invention, the heterocycle-modified glycerin fatty acid ester of the present invention can be produced.

DESCRIPTION OF EMBODIMENTS

Embodiments of the present invention will be described in detail below.

Note that in the present specification, numerical ranges indicated using "(from) . . . to . . . " include the former number as the lower limit value and the latter number as the upper limit value.

In the present specification, unless otherwise noted, a single corresponding substance may be used for each component, or a combination of two or more types of corresponding substances may be used for each component. When a component contains two or more types of substances, the content of the component means the total content of the two or more types of substances.

In the present specification, the production method of each component is not particularly limited unless otherwise noted. Examples thereof include known methods.

Heterocycle-Modified Glycerin Fatty Acid Ester

The heterocycle-modified glycerin fatty acid ester according to an embodiment of the present invention (compound according to an embodiment of the present invention) is a heterocycle-modified glycerin fatty acid ester, where an epoxy group is modified with a heterocyclic compound having a heterocycle having at least one H—N< bond;

the heterocycle is at least one selected from the group consisting of a piperazine ring, a morpholine ring, and a thiomorpholine ring; and the heterocycle may have a substituent.

The compound according to an embodiment of the present invention is thought to achieve desired effects as a result of having such a configuration. Although the reason is not clear, it is assumed to be as follows.

The compound according to an embodiment of the present invention has a backbone constituted by a glycerin fatty acid ester, and the fatty acid constituting the backbone has an aliphatic hydrocarbon group as a main chain backbone (the aliphatic hydrocarbon group includes a saturated aliphatic hydrocarbon group and/or unsaturated aliphatic hydrocarbon group). Thus, the compound according to an embodiment of the present invention has hydrophobicity.

Furthermore, because the compound according to an embodiment of the present invention has a heterocycle, the compound according to an embodiment of the present invention has hydrophilicity.

As described above, it is conceived that, in the case where the compound according to an embodiment of the present invention having the hydrophobicity and the hydrophilicity is added to a rubber composition containing a rubber and silica, the compound according to an embodiment of the present invention tends to interact with the rubber due to the hydrophobicity, and the compound according to an embodiment of the present invention tends to interact with the silica due to the hydrophilicity.

Therefore, it is conceived that the compound according to an embodiment of the present invention functions like a surfactant in the rubber composition containing the rubber and the silica, and can enhance dispersibility of the silica in the rubber.

Furthermore, it is conceived that the compound according to an embodiment of the present invention tends to enter in between rubber molecules due to the hydrophobicity and can disorganize the molecular arrangement of the rubber molecules by entering in between the rubber molecules.

The present inventors presume that, because the compound according to an embodiment of the present invention has excellent dispersibility of silica in rubber and can disorganize the molecular arrangement of rubber molecules as described above, a rubber composition containing the compound according to an embodiment of the present invention makes the Mooney viscosity of an unvulcanized rubber low.

Furthermore, the present inventors presume that, because the compound according to an embodiment of the present invention is less likely to form chemical bonds with rubber and/or silica and does not have excessively high vulcanization acceleration effect, the compound according to an embodiment of the present invention can suppress scorch (burning) of the rubber composition.

As described above, it is conceived that, because the Mooney viscosity of a rubber composition is made low and scorch is suppressed according to the compound of an embodiment of the present invention, a rubber composition using the compound according to an embodiment of the present invention for rubber and silica (composition according to an embodiment of the present invention) achieves excellent processability.

The present invention is described in detail below.

Modification

In the compound according to an embodiment of the present invention, an epoxy group is modified with a heterocyclic compound having a heterocycle having at least one H—N< bond.

In an embodiment of the present invention, the heterocyclic compound can function as a modifying agent for the epoxy group.

Reaction of Modification

In an embodiment of the present invention, the epoxy group reacts with the H—N< bond in the heterocycle, and is modified with the heterocycle.

Modified Group

The compound according to an embodiment of the present invention may have a modified group, in which the epoxy group is modified with the heterocycle.

The modified group has a heterocycle originated from the heterocyclic compound.

The modified group may further have, besides the heterocycle, for example, a hydroxy group. The hydroxy group may be, for example, generated by ring-opening of the epoxy group. It is conceived that the hydroxy group can contribute to the dispersion of silica.

Examples of the modified group include a group represented by Formula (III) below.

The epoxy group is modified, according to the reaction formula below, to be a group represented by Formula (III) below for example.

[Chemical Formula 2]

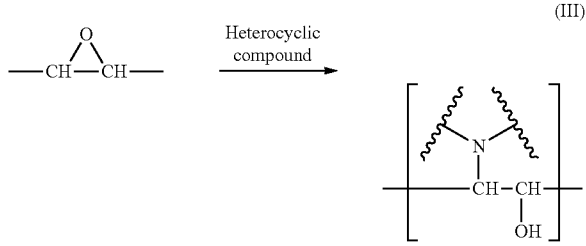

In Formula (III), the hydroxy group is a hydroxy group generated by ring-opening of the epoxy group, and the nitrogen atom is a nitrogen atom derived from the aforementioned N—H< bond.

The heterocyclic compound shown in the reaction formula above is the same as the heterocyclic compound in an embodiment of the present invention. The heterocycle contained in the heterocyclic compound shown in the reaction formula is at least one selected from the group consisting of a piperazine ring, a morpholine ring, and a thiomorpholine ring. Furthermore, the heterocycle may have a substituent. The substituent is not particularly limited.

Note that, in the case where the heterocycle is a piperazine ring, one piperazine ring preferably forms one group represented by Formula (III) above from the perspective of achieving superior processability.

Group Represented by Formula (I)

Specific examples of the group represented by Formula (III) include a group represented by Formula (I) below.

[Chemical Formula 3]

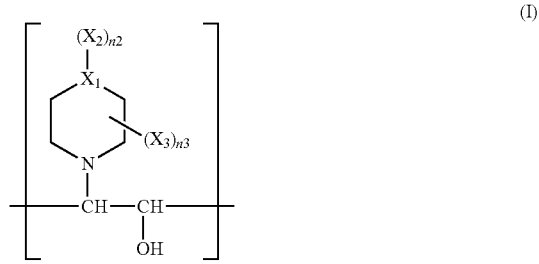

In Formula (I), $X_1$ represents at least one selected from the group consisting of a nitrogen atom, an oxygen atom, and a sulfur atom, $X_3$ represents a hydrocarbon group, and n3 represents from 0 to 4.

Case Where $X_1$ is Nitrogen Atom

In the case where $X_1$ is a nitrogen atom, n2 is 1, and $X_2$ represents a hydrogen atom or an organic group.

Examples of the organic group include sulfone-based protecting groups, carbamate-based protecting groups, and Formula (I-1): —$(R—O)_{n4}$—H. In Formula (I-1), R each independently represents a divalent hydrocarbon group, and n4 represents from 1 to 10.

From the perspective of achieving superior processability, $X_2$ is preferably at least one selected from the group consisting of a hydrogen atom, a sulfone-based protecting group, a carbamate-based protecting group, and the group represented by Formula (I-1) above, and more preferably at least one selected from the group consisting of a sulfone-based protecting group, a carbamate-based protecting group, and the group represented by Formula (I-1) above.

Sulfone-Based Protecting Group

Examples of the sulfone-based protecting group include a methanesulfonyl group, a tosyl group, and a nosyl group.

Carbamate-Based Protecting Group

Examples of the carbamate-based protecting group include a tert-butoxycarbonyl group, an allyloxycarbonyl group, a benzyloxycarbonyl group, and a 9-fluorenylmethyloxycarbonyl group.

Group Represented by Formula (I-1)

In Formula (I-1): —$(R—O)_{n4}$—H, R each independently represents a divalent hydrocarbon group.

In Formula (I-1), the number of carbons of the divalent hydrocarbon group as R is preferably from 2 to 3.

The divalent hydrocarbon group is preferably an aliphatic hydrocarbon group. The aliphatic hydrocarbon group may be linear, branched, cyclic types or any combination thereof.

Examples of the divalent hydrocarbon group include an ethylene group, a propylene group, and a trimethylene group.

In Formula (I-1), n4 represents from 1 to 10, and preferably from 1 to 5.

Case Where $X_1$ is Oxygen Atom or Sulfur Atom

In Formula (I), in the case where $X_1$ is an oxygen atom or a sulfur atom, n2 represents 0.

$X_3$

In Formula (I), the hydrocarbon group as $X_3$ is not particularly limited.

In the case where the group represented by Formula (I) has $X_3$ (n3 is from 1 to 4), the hydrocarbon group is preferably formed only from carbon atom(s) and hydrogen atom(s) from the perspective of achieving superior processability.

From the perspective of achieving superior processability, n3 is preferably 0.

Backbone

The compound according to an embodiment of the present invention may have a glycerin fatty acid ester as its backbone.

The glycerin fatty acid ester as the backbone is not particularly limited as long as the glycerin fatty acid ester is an ester of glycerin and a fatty acid. Examples of the glycerin fatty acid ester include glycerin fatty acid monoesters, glycerin fatty acid diesters, and glycerin fatty acid triesters.

In the case where the glycerin fatty acid ester as the backbone is a glycerin fatty acid diester or a glycerin fatty acid triester, a plurality of fatty acids constituting the glycerin fatty acid ester may be the same or different.

From the perspective of achieving superior processability, the backbone is preferably a glycerin fatty acid triester.

Fatty Acid Constituting Backbone

The fatty acid constituting the backbone may have an aliphatic hydrocarbon group. The aliphatic hydrocarbon group may be saturated or unsaturated. An example of a preferable aspect is one in which the aliphatic hydrocarbon group is saturated. The aliphatic hydrocarbon group may further contain an epoxy group.

The number of carbons of the aliphatic hydrocarbon group contained in the fatty acid (other than the carbon constituting a carboxy group) is preferably from 6 to 24.

Glycerin Constituting Backbone

The glycerin constituting the backbone is not particularly limited. Examples of the glycerin include glycerin ($C_3H_8O_3$) and polyglycerin.

The glycerin constituting the backbone is preferably glycerin ($C_3H_8O_3$).

An example of a preferable aspect is one in which the glycerin fatty acid ester constituting the backbone of the compound according to an embodiment of the present invention is derived from an epoxidized glycerin fatty acid ester described below.

Modified Group and Backbone

The compound according to an embodiment of the present invention may have the modified group and the backbone.

An example of a preferable aspect is one in which the modified group is bonded to the aliphatic hydrocarbon group in the backbone described above.

Examples of the bonding between the modified group and the backbone include aspects where the modified group constitutes a part of the main chain of the aliphatic hydrocarbon group.

When the aspect described above is described using, as an example, a group represented by Formula (III) above as the modified group, —CH—CH(OH)— in Formula (III) above constitutes a part of the main chain of the aliphatic hydrocarbon group.

The position of the modified group in the backbone is not particularly limited. The position of the modified group can correspond to, for example, the position of the epoxy group in the epoxidized glycerin fatty acid ester described below.

In the compound according to an embodiment of the present invention, the fatty acid (the aliphatic hydrocarbon group in the fatty acid) constituting the heterocycle-modified glycerin fatty acid ester preferably has a group represented by Formula (III) (specifically, for example, group represented by Formula (I)).

The compound according to an embodiment of the present invention is described using the compound represented by (IV) below as an example of the compound according to an embodiment of the present invention.

The compound represented by (IV) below is an example of the heterocycle-modified glycerin fatty acid ester in which epoxy groups contained in an epoxidized substance of glycerin oleic acid triester (all unsaturated bonds in the glycerin oleic acid triester are epoxidized) are modified with the heterocyclic compounds (the heterocycles).

[Chemical Formula 4]

(IV)

In Formula (IV),
a group represented by

[Chemical Formula 5]

represents, a group, derived from the heterocyclic compound, by heterocycle that may have a substituent, in the abbreviated form. The nitrogen atom shown in the formula above is a nitrogen atom derived from the aforementioned N—H< bond.

In Formula (IV), all the epoxy groups are modified with the heterocyclic compounds; however, in an embodiment of the present invention, at least one or some of the epoxy groups have only to be modified with the heterocyclic compound(s).

In Formula (IV), Cx represents a carbon atom to which the heterocycle is bonded, and Cy represents a carbon atom to which a hydroxy group generated by ring-opening of the epoxy group is bonded.

The hetero ring may bond to the carbon atom Cy, and the hydroxy group may bond to the carbon atom Cx.

As described above, in an embodiment of the present invention, the carbon atom to which the heterocycle is bonded and the carbon atom to which the hydroxy group is bonded may be replaced.

From the perspective of achieving superior processability, the compound according to an embodiment of the present invention may have, on average, preferably from 1 to 8, and more preferably from 3 to 8, of the heterocycles per one molecule.

The compound according to an embodiment of the present invention may have an unreacted epoxy group in one molecule.

The compound according to an embodiment of the present invention may have, on average, from 0 to 7 epoxy groups per one molecule.

The epoxy group may be derived from, for example, a raw material (e.g. epoxidized glycerin fatty acid ester).

The compound according to an embodiment of the present invention may be a mixture.

Furthermore, the compound according to an embodiment of the present invention may further contain, for example, an unmodified epoxidized glycerin fatty acid ester and/or an unreacted heterocyclic compound.

Heterocyclic Compound

In an embodiment of the present invention, the heterocyclic compound used to modify the epoxy group is a compound having a heterocycle having at least one H—N< bond.

In an embodiment of the present invention, the heterocycle is at least one selected from the group consisting of a piperazine ring, a morpholine ring, and a thiomorpholine ring, and the heterocycle may have a substituent.

In an embodiment of the present invention, the heterocyclic compound can function as a modifying agent for the epoxy group.

From the perspective of achieving superior processability, the heterocycle is preferably a morpholine ring.

Examples of the heterocyclic compound include a compound represented by Formula (II) below.

[Chemical Formula 6]

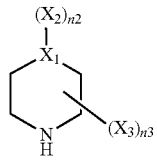

(II)

In Formula (II), $X_1$ represents at least one selected from the group consisting of a nitrogen atom, an oxygen atom, and a sulfur atom, $X_3$ represents a hydrocarbon group, and n3 represents from 0 to 4.

In the case where $X_1$ is a nitrogen atom, n2 is 1, and $X_2$ represents a hydrogen atom or an organic group.

In the case where $X_1$ is an oxygen atom or a sulfur atom, n2 represents 0.

$X_1$ to $X_3$ and n2 and n3 in Formula (II) are respectively the same as $X_1$ to $X_3$ and n2 and n3 in Formula (I).

Specific examples of the heterocyclic compound include piperazine;
piperazine having a group represented by Formula (I-1) above on a nitrogen atom (the nitrogen atom written on the left is the nitrogen atom of $X_1$ in Formula (II); hereinafter the same in this paragraph), such as 1-(2-hydroxyethyl)piperazine;
piperazine having a sulfone-based protecting group on a nitrogen atom;
piperazine having a carbamate-based protecting group on a nitrogen atom;
morpholine; and
thiomorpholine.

Epoxy Group

In an embodiment of the present invention, the epoxy group to be modified may be, for example, derived from an epoxidized glycerin fatty acid ester as a raw material.

Epoxidized Glycerin Fatty Acid Ester

The epoxidized glycerin fatty acid ester is a compound having an epoxy group and having a glycerin fatty acid ester as the backbone.

The glycerin fatty acid ester as the backbone is the same as the glycerin fatty acid ester descried above.

Epoxy Group and Backbone

In the epoxidized glycerin fatty acid ester, an example of a preferable aspect is one in which the epoxy group is bonded to the aliphatic hydrocarbon group in the backbone described above.

Examples of the bonding between the epoxy group and the backbone include aspects where the epoxy group constitutes a part of the main chain of the aliphatic hydrocarbon group.

The position of the epoxy group in the epoxidized glycerin fatty acid ester is not particularly limited. The position of the epoxy group can correspond to, for example, the position of the unsaturated bond (of the unsaturated aliphatic hydrocarbon group contained) in the unsaturated fatty acid constituting the glycerin fatty acid ester containing the unsaturated bond (glycerin unsaturated fatty acid ester) described below.

Examples of the epoxidized glycerin fatty acid ester include epoxidized substances of glycerin unsaturated fatty acid esters.

In the glycerin unsaturated fatty acid ester, any unsaturated bond may be epoxidized, without particular limitation.

Some or all of the unsaturated bonds contained in the glycerin unsaturated fatty acid ester may be epoxidized.

The epoxidized glycerin fatty acid ester may further contain saturated fatty acids, such as myristic acid, palmitic acid, and stearic acid, as fatty acids to constitute the epoxidized glycerin fatty acid ester, besides epoxidized unsaturated fatty acid described above.

Oxirane Oxygen Concentration

The oxirane oxygen concentration of the epoxidized glycerin fatty acid ester (e.g. epoxidized vegetable oil) is preferably from 3 to 10%.

The oxirane oxygen concentration (%) can be determined by chemical titration by the hydrogen bromide method in accordance with (1) 2.3.7.1 of "Standard methods for the analysis of fats, oils and related materials (2013)" by Japan Oil Chemists' Society.

Acid Value

The acid value of the epoxidized glycerin fatty acid ester (e.g. epoxidized vegetable oil) is preferably from 0 to 0.5 KOHmg/g.

In an embodiment of the present invention, the acid value of the epoxidized glycerin fatty acid ester can be measured by the following method.

In an Erlenmeyer flask, a sample (epoxidized glycerin fatty acid ester) is collected. To the sample, from 50 to 100 mL of mixed solvent, in which ethanol and diethyl ether are mixed in the volume ratio of 1:1, is added and shaken well to completely dissolve the sample, thus preparing a mixture solution. Immediately before the use, a few drops of phenolphthalein indicator reagent are added to the mixture, and titration is performed by 0.1 mol/L potassium hydroxide-ethanol solution, which is a titrant. The terminating point of the titration is the time at which a pale red color is maintained for 30 seconds in the case where a phenolphthalein indicator reagent is used as the indicator reagent.

The acid value A of the sample is calculated based on the following equation.

$$A = B \times f \times 5.611/S$$

A: Acid value
B: Amount of 0.1 mol/L potassium hydroxide-ethanol solution used in titration (mL)
f: Factor of 0.1 mol/L potassium hydroxide-ethanol solution
S: Mass of sample (g)

The aforementioned f can be determined, in advance, based on the amount required for neutralization performed by placing 25 mL of 0.1 mol/L hydrochloric acid in an Erlenmeyer flask by using a volumetric pipette, adding a phenolphthalein solution, and titrating with 0.1 mol/L potassium hydroxide-ethanol solution.

Furthermore, as the potassium hydroxide-ethanol solution, a commercially available potassium hydroxide-ethanol solution having the specification value of f from, for example, 0.990 to 1.009 (e.g., test value: 0.997) may be used.

Viscosity

The viscosity at 30° C. of the epoxidized glycerin fatty acid ester (e.g. epoxidized vegetable oil) is preferably from 10 to 2000 mPa·s.

In an embodiment of the present invention, the viscosity is measured by using a cone-and-plate rotating viscometer in accordance with JIS Z 8803.

Examples of the epoxidized glycerin fatty acid ester include epoxidized vegetal oils.

Epoxidized Vegetal Oil

The epoxidized vegetal oil is not particularly limited as long as the epoxidized vegetal oil is epoxidized.

Note that, in the present specification, vegetable oils include oils of vegetables and fats of vegetables.

Examples of the epoxidized vegetal oil include epoxidized substance of vegetable oils, such as soybean oil, linseed oil, rice bran oil, tung oil, sesame oil, coconut oil, castor oil, safflower oil, corn oil, cottonseed oil, palm oil, sunflower oil, almond oil, cashew nut oil, hazelnut oil, olive oil, grapeseed oil, rapeseed oil, and pine nut oil.

Among these, the epoxidized vegetal oil is preferably an epoxidized soybean oil or an epoxidized linseed oil from the perspective of achieving superior processability.

The vegetable oil, which is the raw material of the epoxidized vegetal oil, is typically a mixture of glycerin fatty acid esters of a combination of various fatty acids. Thus, the epoxidized vegetal oil obtained by epoxidizing the vegetable oil may be a mixture of various epoxidized glycerin fatty acid esters.

Note that the epoxidized vegetal oil may further contain unepoxidized or insufficiently epoxidized vegetal oils.

Production Method for Epoxidized Glycerin Fatty Acid Ester

The production method for the epoxidized glycerin fatty acid ester is not particularly limited.

Examples of the production method include a method that epoxidizes a glycerin unsaturated fatty acid ester.

The glycerin unsaturated fatty acid ester used as the raw material in the production method is not particularly limited as long as the glycerin unsaturated fatty acid ester is an ester of an unsaturated fatty acid as a fatty acid and glycerin.

Examples of the unsaturated fatty acid include monounsaturated fatty acids, such as parmitoleic acid, oleic acid, vaccenic acid, and eicosenoic acid; and polyunsaturated fatty acids, such as linoleic acid and linolenic acid.

The glycerin unsaturated fatty acid ester may further contain saturated fatty acids, such as myristic acid, palmitic acid, stearic acid, arachidic acid, behenic acid, and lignoceric acid, as fatty acids to constitute the glycerin unsaturated fatty acid ester, besides the unsaturated fatty acid described above.

Use

The compound according to an embodiment of the present invention can be used, for example, as a compounding agent for rubber.

Production Method for Heterocycle-Modified Glycerin Fatty Acid Ester

The production method for the heterocycle-modified glycerin fatty acid ester according to an embodiment of the present invention (the production method according to an embodiment of the present invention) is a production method for a heterocycle-modified glycerin fatty acid ester, where the heterocycle-modified glycerin fatty acid ester according to an embodiment of the present invention is produced by reacting an epoxidized glycerin fatty acid ester and the heterocyclic compound.

The epoxidized glycerin fatty acid ester used in the production method according to an embodiment of the present invention is not particularly limited. Examples thereof include the groups listed above.

The heterocyclic compound used in the production method according to an embodiment of the present invention is the same as the heterocyclic compound described above.

The used amount of the heterocyclic compound is preferably from 0.1 to 1.0 molar equivalent, and more preferably from 0.2 to 1.0 molar equivalent, relative to the amount of the epoxy group contained in the epoxidized glycerin fatty acid ester (or the epoxidized vegetal oil).

Specifically, for example, as the production method according to an embodiment of the present invention, the heterocycle-modified glycerin fatty acid ester according to an embodiment of the present invention can be produced by mixing the epoxidized glycerin fatty acid ester and the heterocyclic compound and reacting them at, for example, 100 to 150° C.

In the reaction described above, for example, a catalyst or a solvent may be further used.

Degree of Modification

In an embodiment of the present invention, the degree of modification of modifying the epoxy group with the heterocycle (heterocycle/epoxy group) is preferably from 20 to 100 mol %, and more preferably from 80 to 100 mol % from the perspective of achieving superior processability.

In an embodiment of the present invention, the degree of modification is calculated based on an area ratio of peaks of the heterocycle and the epoxy group of a chart obtained by analyzing the compound according to an embodiment of the present invention by $^1$H-NMR.

Rubber Composition

The rubber composition according to an embodiment of the present invention (composition according to an embodiment of the present invention) is a rubber composition containing:

a rubber;

silica; and a heterocycle-modified glycerin fatty acid ester, in which an epoxy group is modified with a heterocyclic compound having a heterocycle having at least one H—N< bond, where the heterocycle is at least one selected from the group consisting of a piperazine ring, a morpholine ring, and a thiomorpholine ring; and the heterocycle may have a substituent.

Rubber

The rubber contained in the composition according to an embodiment of the present invention is not particularly limited. Examples of the rubber include diene rubbers, such as a natural rubber (NR), a butadiene rubber, an isoprene rubber (IR), an aromatic vinyl-conjugated diene copolymer rubber such as a styrene butadiene rubber, an acrylonitrile-butadiene copolymer rubber (NBR), a butyl rubber (IIR), a halogenated butyl rubber (Br-IIR and Cl-IIR), and a chloroprene rubber (CR).

A part or all of the rubber may be the diene rubber described above.

Among those, the rubber is preferably an aromatic vinyl-conjugated diene copolymer rubber and/or a butadiene rubber from the perspective of excellent low heat buildup and excellent strength characteristics.

The weight average molecular weight of the rubber can be, for example, from 100000 to 3000000. In an embodiment of the present invention, the weight average molecular weight (Mw) of the rubber is measured by gel permeation chromatography (GPC), based on calibration with polystyrene standard using tetrahydrofuran as a solvent.

Silica

The silica included in the composition according to an embodiment of the present invention is not particularly limited.

Examples of the silica include fumed silica, calcined silica, precipitated silica, pulverized silica, molten silica, and colloidal silica.

The BET specific surface area of the silica is preferably from 150 to 300 m$^2$/g from the perspective of achieving excellent low heat buildup. The BET specific surface area of the silica is to be measured in accordance with a Brunauer-Emmett-Teller method corresponding to Annex D of ISO 5794/1.

Content of Silica

From the perspective of achieving superior low heat buildup, the content of the silica is preferably from 50 to 200 parts by mass, and more preferably from 70 to 150 parts by mass, per 100 parts by mass of the rubber.

Heterocycle-Modified Glycerin Fatty Acid Ester

The heterocycle-modified glycerin fatty acid ester contained in the composition according to an embodiment of the present invention is not particularly limited as long as the heterocycle-modified glycerin fatty acid ester is the heterocycle-modified glycerin fatty acid ester according to an embodiment of the present invention.

Content of Heterocycle-Modified Glycerin Fatty Acid Ester

From the perspective of achieving superior processability, the content of the heterocycle-modified glycerin fatty acid ester is preferably from 1 to 30 parts by mass, and more preferably from 1 to 15 parts by mass, per 100 parts by mass of the rubber.

Additives

The composition according to an embodiment of the present invention may further contain additives as necessary within a scope that does not impair the effect or purpose thereof. Examples of the additive include those generally used in rubber compositions, such as fillers other than silica (e.g., carbon black), silane coupling agents (e.g., silane coupling agent containing sulfur), vulcanization accelerators, resins, zinc oxide, stearic acid, anti-aging agents, processing aids, oils, vulcanizing agents such as sulfur, and peroxides. The content of the additive can be appropriately selected.

Carbon Black

The composition according to an embodiment of the present invention preferably further contains carbon black.

The carbon black is not particularly limited. For example, as the carbon black, various grades of carbon black can be used, such as Super Abrasion Furnace (SAF; hereinafter the same)-High Structure (HS; hereinafter the same), SAF, Intermediate Super Abrasion Furnace (ISAF; hereinafter the same)-HS, ISAF, ISAF-Low Structure (LS; hereinafter the same), Intermediate ISAF (IISAF)-HS, High Abrasion Furnace (HAF; hereinafter the same)-HS, HAF, HAF-LS, and Fast Extruding Furnace (FEF).

The nitrogen adsorption specific surface area (N$_2$SA) of the carbon black is preferably from 50 to 200 m$^2$/g from the perspective of achieving superior processability. The nitrogen adsorption specific surface area of the carbon black is measured in accordance with JIS K 6217-2.

The content of the carbon black is preferably from 1 to 50 parts by mass, and more preferably from 1 to 20 parts by mass, per 100 parts by mass of the rubber.

Because the composition according to an embodiment of the present invention contains the heterocycle-modified glycerin fatty acid ester (the compound according to an embodiment of the present invention), substantially no silane coupling agent can be used, or the used amount of the silane coupling agent can be reduced.

In an embodiment of the present invention, the content of the silane coupling agent can be from 0 to 20 parts by mass per 100 parts by mass of the rubber from the perspective of achieving superior processability.

In the present specification, substantially no silane coupling agent being used means that the content of the silane coupling agent is from 0 to 1.0 part by mass per 100 parts by mass of the rubber.

The silane coupling agent is not particularly limited as long as the silane coupling agent is a compound having a silyl group that can interact with fillers (e.g. silica, carbon black) and a functional group that can interact with rubber.

The silyl group is a group having a silicon atom. Examples of the silyl group include alkoxysilyl groups and silanol groups.

Examples of the functional group include sulfide bonds, polysulfide bonds, a mercapto group, a thiocarbonyl group, a hydroxy group, an amino group, an imino group, and a carboxy group.

The bond between the silyl group and the functional group is not particularly limited.

Examples of the silane coupling agent include silane coupling agents containing sulfur; and silane coupling agents containing a hydroxy group, an amino group, an imino group, or a carboxy group.

Method for Producing Rubber Composition

The production method for the composition according to an embodiment of the present invention is not particularly limited. Specific examples thereof include a method in which the components described above (other than sulfur and vulcanization accelerators) are mixed at 100 to 200° C. using known methods and apparatuses (e.g., a Banbury mixer, a kneader, or a roll) to obtain a mixture, and then the sulfur and the vulcanization accelerators are added to the mixture and further mixed to produce the composition according to an embodiment of the present invention.

In addition, the composition according to an embodiment of the present invention can be vulcanized or crosslinked, for example, under the known vulcanization or crosslinking conditions.

For example, tires, conveyor belts, and hoses can be produced by using the composition according to an embodiment of the present invention.

EXAMPLE

The present invention is described below in detail using examples but the present invention is not limited to such examples.

Synthesis of Heterocycle-Modified Glycerin Fatty Acid Ester 1

A heterocycle-modified glycerin fatty acid ester 1 was obtained by reacting 13.9 g of 1-(2-hydroxyethyl)piperazine (hydroxyethylpiperazine, available from Nippon Nyukazai Co., Ltd.) and 50.0 g of epoxidized soybean oil (ADK CIZER O-130P, available from Adeka Corporation) at 100° C. for 12 hours.

The heterocycle-modified glycerin fatty acid ester 1 had, on average, 2.0 heterocycles and 2.0 epoxy groups per one molecule.

The amount of the 1-(2-hydroxyethyl)piperazine was 0.5 molar equivalent relative to the amount of the epoxy group contained in the epoxidized soybean oil.

The physical properties of the ADK CIZER O-130P were as follows.

Oxirane oxygen concentration: 6.7%
Acid value: 0.3 KOHmg/g
Viscosity at 30° C.: 280 mPa·s Synthesis of Heterocycle-Modified Glycerin Fatty Acid Ester 2

A heterocycle-modified glycerin fatty acid ester 2 was obtained by reacting 27.7 g of 1-(2-hydroxyethyl)piperazine (hydroxyethylpiperazine, available from Nippon Nyukazai Co., Ltd.) and 50.0 g of epoxidized soybean oil (ADK CIZER O-130P, available from Adeka Corporation) at 100° C. for 12 hours.

The heterocycle-modified glycerin fatty acid ester 2 had, on average, 4.0 heterocycles per one molecule. The heterocycle-modified glycerin fatty acid ester 2 had no epoxy groups.

The amount of the 1-(2-hydroxyethyl)piperazine was 1.0 molar equivalent relative to the amount of the epoxy group contained in the epoxidized soybean oil.

Synthesis of Heterocycle-Modified Glycerin Fatty Acid Ester 3

A heterocycle-modified glycerin fatty acid ester 3 was obtained by reacting 37.6 g of 1-(2-hydroxyethyl)piperazine (hydroxyethylpiperazine, available from Nippon Nyukazai Co., Ltd.) and 50.0 g of epoxidized linseed oil (ADK CIZER O-180A, available from Adeka Corporation) at 100° C. for 12 hours.

The heterocycle-modified glycerin fatty acid ester 3 had, on average, 5.6 heterocycles per one molecule. The heterocycle-modified glycerin fatty acid ester 3 had no epoxy groups.

The amount of the 1-(2-hydroxyethyl)piperazine was 1.0 molar equivalent relative to the amount of the epoxy group contained in the epoxidized linseed oil.

The physical properties of the ADK CIZER O-180A were as follows.

Oxirane oxygen concentration: 9.1%
Acid value: 0.3 KOHmg/g
Viscosity at 30° C.: 650 mPa·s Synthesis of Heterocycle-Modified Glycerin Fatty Acid Ester 4

A heterocycle-modified glycerin fatty acid ester 4 was obtained by reacting 25.2 g of morpholine (available from Tokyo Chemical Industry Co., Ltd.) and 50.0 g of epoxidized linseed oil (ADK CIZER O-180A, available from Adeka Corporation) at 100° C. for 12 hours.

The heterocycle-modified glycerin fatty acid ester 4 had, on average, 5.6 heterocycles per one molecule. The heterocycle-modified glycerin fatty acid ester 4 had no epoxy groups.

The amount of the morpholine was 1.0 molar equivalent relative to the amount of the epoxy group contained in the epoxidized linseed oil.

Note that the heterocycle-modified glycerin fatty acid esters 1 to 4 had no unsaturated bonds in the aliphatic hydrocarbon groups contained in the fatty acids constituting the heterocycle-modified glycerin fatty acid esters 1 to 4.

Production of the Rubber Composition

The components shown in Table 1 below were used in compositions (part by mass) shown in the same table.

Specifically, a mixture was obtained by heating the components shown in Table 1 below, other than the sulfur and the vulcanization accelerators, in a 1.7 L closed-type Banbury mixer to a temperature approximately 150° C., mixing the mixture for 5 minutes, then discharging the mixture, and cooling it to room temperature. The sulfur and the vulcanization accelerators were then mixed into the mixture obtained as described above using the Banbury mixer described above to produce a rubber composition.

Note that, in Table 1, the blended amount of the SBR was the amount of the rubber (oil extended product) (unit: part by mass). The net content of the SBR in 110 parts by mass of the oil extended SBR was 80 parts by mass.

Evaluation

The following evaluations were performed by using the rubber compositions produced as described above. The results are shown in Table 1. In Table 1, for each evaluation item, evaluation result of each of the examples was shown as an index value relative to the evaluation result (100) of Standard Example 1.

Mooney Viscosity

For each of the rubber compositions (unvulcanized) produced as described above, according to JIS K 6300-1: 2013, Mooney viscosity ($ML_{1+4}$) was measured using an L-shaped rotor under the conditions that the preheating time was 1 minute, the rotation time of the rotor was 4 minutes, and the test temperature was 100° C.

In an embodiment of the present invention, the case where the index value of the Mooney viscosity was 90 or less was evaluated as achieving excellent processability. Furthermore, a smaller index value of the Mooney viscosity indicated lower Mooney viscosity and superior processability.

Mooney Scorch

For each of the rubber compositions (unvulcanized) produced as described above, according to JIS K 6300-1: 2013, a scorch time was measured using the L-shaped rotor at a test temperature of 125° C.

In an embodiment of the present invention, when the Mooney scorch index is from 90 to 105, the scorch time is long, the scorch resistance is superior, and the workability is superior.

TABLE 1

|  | Standard Example | Example | | | | | Comparative Example | |
| --- | --- | --- | --- | --- | --- | --- | --- | --- |
|  | 1 | 1 | 2 | 3 | 4 | 5 | 1 | 2 |
| SBR *1 | 110.0 | 110.0 | 110.0 | 110.0 | 110.0 | 110.0 | 110.0 | 110.0 |
| BR *2 | 20.0 | 20.0 | 20.0 | 20.0 | 20.0 | 20.0 | 20.0 | 20.0 |
| Silica 1 *3 | 90.0 | 90.0 | 90.0 | 90.0 | 90.0 | 90.0 | 90.0 | 90.0 |
| Carbon black *4 | 5.0 | 5.0 | 5.0 | 5.0 | 5.0 | 5.0 | 5.0 | 5.0 |
| Silane coupling agent *5 | 6.3 | 6.3 | 6.3 | 6.3 | 6.3 |  | 11.7 | 7.2 |
| Zinc oxide *6 | 3.0 | 3.0 | 3.0 | 3.0 | 3.0 | 3.0 | 3.0 | 3.0 |
| Stearic acid *7 | 2.0 | 2.0 | 2.0 | 2.0 | 2.0 | 2.0 | 2.0 | 2.0 |
| Anti-aging agent *8 | 1.5 | 1.5 | 1.5 | 1.5 | 1.5 | 1.5 | 1.5 | 1.5 |
| Process oil *9 | 15.0 | 15.0 | 15.0 | 15.0 | 15.0 | 15.0 | 15.0 | 15.0 |
| Heterocycle-modified glycerin fatty acid ester 1 *10 |  | 5.4 |  |  |  | 11.7 |  |  |
| Heterocycle-modified glycerin fatty acid ester 2 *11 |  |  | 5.4 |  |  |  |  |  |

TABLE 1-continued

|  | Standard Example 1 | Example 1 | Example 2 | Example 3 | Example 4 | Example 5 | Comparative Example 1 | Comparative Example 2 |
|---|---|---|---|---|---|---|---|---|
| Heterocycle-modified glycerin fatty acid ester 3 *12 |  |  |  | 5.4 |  |  |  |  |
| Heterocycle-modified glycerin fatty acid ester 4 *13 |  |  |  |  | 5.4 |  |  |  |
| (Comparative) Heterocyclic compound 5 *14 |  |  |  |  |  |  |  | 5.4 |
| Sulfur *15 | 1.4 | 1.4 | 1.4 | 1.4 | 1.4 | 1.4 | 1.4 | 1.4 |
| Vulcanization accelerator 1 *16 | 1.7 | 1.7 | 1.7 | 1.7 | 1.7 | 1.7 | 1.7 | 1.7 |
| Vulcanization accelerator 2 *17 | 0.4 | 0.4 | 0.4 | 0.4 | 0.4 | 0.4 | 0.4 | 0.4 |
| Mooney viscosity | 100 | 88 | 85 | 86 | 85 | 84 | 91 | 96 |
| Mooney scorch | 100 | 96 | 93 | 94 | 90 | 94 | 63 | 82 |

Details of the components described in Table 1 are as follows.

*1: SBR (Tufdene 3830, available from Asahi Kasei Corporation, oil extender content=37.5 parts by mass per 100 parts by mass of net amount of SBR), styrene butadiene rubber

*2: BR (Nipol BR1220, available from Zeon Corporation.), butadiene rubber

*3: Silica 1 (Zeosil 1165MP, available from Rhodia Ltd., BET specific surface area=165 $m^2/g$)

*4: Carbon black (Show Black N339, available from Cabot Corporation., nitrogen adsorption specific surface area ($N_2SA$)=90 $m^2/g$)

*5: Silane coupling agent (Si69, available from Evonik Degussa; bis (3-triexothysilylpropyl)tetrasulfide)

*6: Zinc oxide (Zinc Oxide III, available from SEIDO CHEMICAL INDUSTRY CO., LTD.)

*7: Stearic acid (Stearic acid YR, available from NOF CORPORATION)

*8: Anti-aging agent (Santoflex 6PPD, available from Solutia Europe)

*9: Process oil (Extract No. 4 S, available from Showa Shell Sekiyu K.K.)

*10: Heterocycle-modified glycerin fatty acid ester 1 (heterocycle-modified glycerin fatty acid ester 1 synthesized as described above)

*11: Heterocycle-modified glycerin fatty acid ester 2 (heterocycle-modified glycerin fatty acid ester 2 synthesized as described above)

*12: Heterocycle-modified glycerin fatty acid ester 3 (heterocycle-modified glycerin fatty acid ester 3 synthesized as described above)

*13: Heterocycle-modified glycerin fatty acid ester 4 (heterocycle-modified glycerin fatty acid ester 4 synthesized as described above)

*14: (Comparative) Heterocyclic compound 5 (reagent [3-(1-piperazinyl)propyl]triexothysilane)

*15: Sulfur (oil-treated sulfur, available from Karuizawa Refinery Ltd.)

*16: Vulcanization accelerator 1 (Nocceler CZ-G, available from Ouchi Shinko Chemical Industrial Co., Ltd.)

*17: Vulcanization accelerator 2 (Perkacity DPG, available from Flexsys)

As is clear from the results shown in Table 1, Comparative Example 1, which contained no predetermined heterocycle-modified glycerin fatty acid ester similarly to Standard Example 1 and had a greater content of the silane coupling agent compared to that of Standard Example 1, had a high Mooney viscosity, a short scorch time, and poor processability.

Comparative Example 2, which contained no predetermined heterocycle-modified glycerin fatty acid ester but, instead, contained [3-(1-piperazinyl)propyl]triethoxysilane, had a high Mooney viscosity, a short scorch time, and poor processability.

On the other hand, each of the rubber compositions according to embodiments of the present invention achieved a low Mooney viscosity, an appropriate range of scorch time, and excellent processability.

The invention claimed is:

1. A rubber composition comprising:
   a rubber;
   silica; and
   a heterocycle-modified glycerin fatty acid ester, in which an epoxy group is modified with a heterocyclic compound having a heterocycle having at least one H—N<bond, wherein
   the heterocycle is at least one selected from the group consisting of a piperazine ring, a morpholine ring, and a thiomorpholine ring; and
   the heterocycle may have a substituent.

2. The rubber composition according to claim 1, wherein the heterocycle-modified glycerin fatty acid ester has a group represented by Formula (I) below:

[Chemical Formula 1]

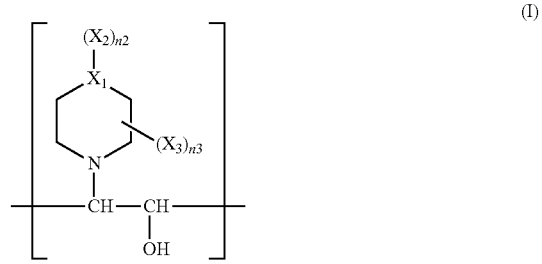

(I)

where $X_1$ represents at least one selected from the group consisting of a nitrogen atom, an oxygen atom, and a sulfur atom, $X_3$ represents a hydrocarbon group, and n3 represents from 0 to 4, in the case where $X_1$ is a nitrogen atom, n2 is 1, and $X_2$ represents a hydrogen atom or an organic group, and in the case where $X_1$ is an oxygen atom or a sulfur atom, n2 represents 0.

3. The rubber composition according to claim 2, wherein,
in Formula (I), $X_1$ is a nitrogen atom,
n2 is 1, and $X_2$ is at least one selected from the group consisting of a hydrogen atom, a sulfone-based protecting group, a carbamate-based protecting group, and Formula (I-1): —$(R-O)_{n4}$—H; and
in Formula (I-1), R each independently represents a divalent hydrocarbon group, and n4 represents from 1 to 10.

4. The rubber composition according to claim 2, wherein, in Formula (I), $X_1$ is an oxygen atom or a sulfur atom, and n2 is 0.

5. The rubber composition according to claim 2, wherein a fatty acid constituting the heterocycle-modified glycerin fatty acid ester has a group represented by Formula (I).

* * * * *